US00PP13508P2

(12) United States Plant Patent
Bergman

(10) Patent No.: US PP13,508 P2
(45) Date of Patent: Jan. 21, 2003

(54) CHRYSANTHEMUM PLANT NAMED 'WHITE YOGRACELAND'

(75) Inventor: Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/955,841

(22) Filed: Sep. 20, 2001

(51) Int. Cl.[7] ..... A01H 5/00
(52) U.S. Cl. ..... Plt./294
(58) Field of Search ..... Plt./294

*Primary Examiner*—Bruce R. Campell
*Assistant Examiner*—Anne Marie Grünberg
(74) *Attorney, Agent, or Firm*—C. A. Whealy

(57) ABSTRACT

A distinct cultivar of Chrysanthemum plant named 'White Yograceland' characterized by its uniform, upright and outwardly spreading plant habit; strong, dark green foliage; uniform flowering response; early flowering, eight-week response time; large daisy-type inflorescences that are about 11.7 cm in diameter with large anemone centers; white-colored ray and white-colored disc florets with bright yellow apices; and good postproduction longevity with plants maintaining good substance and color for about three or four weeks in an interior environment.

2 Drawing Sheets

BACKGROUND OF THE INVENTION

The present Invention relates to a new and distinct cultivar of Chrysanthemum plant, botanically known as *Chrysanthemum×morifolium* and hereinafter referred to by the name 'White Yograceland'.

The new Chrysanthemum is a product of a planned breeding program conducted by the Inventor in Fort Myers, Fla. The objective of the breeding program is to create new potted Chrysanthemum cultivars that are suitable for year-round production with uniform plant growth habit, good vigor, desirable inflorescence form and floret colors, fast response time, and good postproduction longevity.

The new Chrysanthemum originated by exposing unrooted cuttings of Chrysanthemum cultivar Yograceland, disclosed in U.S. Plant Pat. Ser. No. 12,512 to X-ray radiation in October, 1998 in Fort Myers, Fla. Following the radiation treatment, the cuttings were rooted and terminal apices were removed (pinched) three times to promote lateral branch development. After lateral branches from the third pinch reached sufficient size, terminal cuttings were harvested, planted and flowered in a controlled environment in Fort Myers, Fla. The new Chrysanthemum was discovered and selected by the Inventor as a single flowering plant within this population in April, 1999 in Fort Myers, Fla. The selection of this plant was based on its uniform plant growth habit, good vigor, desirable inflorescence form and floret colors, fast response time, and good postproduction longevity.

Asexual reproduction of the new Chrysanthemum by vegetative tip cuttings was first conducted in Fort Myers, Fla. in July, 1999. Asexual reproduction by cuttings has shown that the unique features of this new Chrysanthemum are stable and reproduced true to type in successive generations.

SUMMARY OF THE INVENTION

The cultivar White Yograceland has not been observed under all possible environmental conditions. The phenotype may vary somewhat with variations in environment such as temperature, daylength, and/or light level, without, however, any variance in genotype.

The following traits have been repeatedly observed and are determined to be the unique characteristics of 'White Yograceland'. These characteristics in combination distinguish 'White Yograceland' as a new and distinct Chrysanthemum:

1. Uniform, upright and outwardly spreading plant habit.
2. Strong, dark green foliage.
3. Uniform flowering response.
4. Can be grown as a disbud or as a spray-type.
5. Early flowering, eight-week response time.
6. Large daisy-type inflorescences that are about 11.7 cm in diameter with large anemone centers.
7. White-colored ray and white-colored disc florets with bright yellow-colored apices.
8. Good postproduction longevity with plants maintaining good substance and color for about three or four weeks in an interior environment.

Plants of the new Chrysanthemum can be compared to plants of the cultivar Yograceland. In side-by-side comparisons conducted by the Inventor in Salinas, Calif., plants of the new Chrysanthemum differ from plants of the cultivar Yograceland in the following characteristics:

1. Plants of the new Chrysanthemum flower slightly earlier than plants of the cultivar Yograceland.
2. Ray florets of plants of the new Chrysanthemum are white in color whereas ray florets of plants of the cultivar Yograceland are light pink in color.

Plants ofthe new Chrysanthemum can be compared to plants of the Chrysanthemum cultivar White Blush, disclosed in U.S. Plant Pat. No. 9,441. In side-by-side comparisons conducted by the Inventor in Salinas, Calif., plants of the new Chrysanthemum differ from plants of the cultivar White Blush in the following characteristics:

1. Plants of the new Chrysanthemum are more vigorous and larger than plants of the cultivar White Blush.

2. Inflorescences of plants of the new Chrysanthemum are anemone-types whereas inflorescences of plants of the cultivar White Blush are daisy-types.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type. Colors in the photographs may differ from the color values cited in the detailed botanical description which accurately describe the colors of the new Chrysanthemum.

The photograph on the first sheet comprises a side perspective view of a typical flowering plant of 'White Yograceland' grown a spray-type.

The photograph on the second sheet comprises a close-up view of typical inflorescences of 'White Yograceland' grown as a spray-type.

DETAILED BOTANICAL DESCRIPTION

In the following description, color references are made to The Royal Horticultural Society Colour Chart except where general terms of ordinary dictionary significance are used. The following observations and measurements describe plants grown and flowered during the summer in Salinas, Calif., in a fiberglass-covered greenhouse and under conditions which approximate those generally used in commercial potted Chrysanthemum production. During the production of these plants, the following conditions were measured: day temperatures, 21 to 27° C.; night temperatures, 17 to 19° C.; and light levels, 5,000 to 6,000 foot-candles. Four unrooted cuttings were directly stuck in 15-cm containers, exposed to long day/short night conditions, and pinched once about 14 days later. At that time, the photoinductive short day/long night treatments were started. Plants used for this description were grown as spray types. Measurements and numerical values represent averages of typical flowering plants.

Botanical classification: *Chrysanthemum×morifolium* cultivar White Yograceland.

Commercial classification: Daisy-type potted Chrysanthemum with anemone centers.

Parentage: Induced mutation of *Chrysanthemum morifolium* cultivar Yograceland.

Propagation:

*Type.*—Terminal tip cuttings.

*Time to initiate roots.*—About four days at 21° C.

*Time to produce a rooted cutting.*—About ten days at 21° C.

*Root description.*—White, fibrous.

*Rooting habit.*—Freely branching.

Plant description:

*Appearance.*—Herbaceous daisy-type potted Chrysanthemum with anemone centers that can be grown as a disbud-type or as a spray-type. Stems mostly upright and outwardly spreading; uniform crown. Freely branching, about four lateral branches develop after removal of terminal apex (pinching); dense and full plants.

*Plant height.*—About 36 cm.

*Plant width.*—About 48 cm.

*Lateral branches.*—Length: About 30 cm. Diameter: About 5 mm. Internode length: About 1.7 cm. Strength: Strong. Texture: Pubescent. Color: Close to 146A.

*Foliage description.*—Arrangement: Alternate. Quantity of leaves per lateral stem: About 12. Length: About 9.8 cm. Width: About 6.4 cm. Apex: Cuspidate to mucronate. Base: Attenuate with truncate tendencies. Margin: Palmately lobed, sinuses between lateral lobes parallel to divergent. Texture: Upper and lower surfaces with very fine pubescence; veins prominent on lower surface. Color: Young and mature foliage, upper surface: 147A. Young and mature foliage, lower surface: Close to 147B. Venation, upper and lower surfaces: 147B. Petiole length: About 2.1 cm. Petiole diameter: About 3 mm. Petiole color, upper and lower surfaces: Close to 146B to 146C.

Inflorescence description:

*Appearance.*—Daisy-type inflorescence form with elongated oblong-shaped ray florets and large anemone centers. Inflorescences borne on terminals above foliage. Disk and ray florets arranged acropetally on a capitulum. Not fragrant. Can be grown as a disbud or as a spray-type.

*Flowering response.*—Under natural conditions, plants flower in the autumn/winter in the Northern Hemisphere. At other times of the year, inflorescence initiation and development can be induced under short day/long night conditions (at least 13.5 hours of darkness). Early flowering; plants exposed to two weeks of long day/short night conditions followed by photoinductive short day/long night conditions flower about 46 to 51 days later when grown during the winter.

*Postproduction longevity.*—Inflorescences maintain good color and substance for about three or four weeks in an interior environment.

*Quantity of inflorescences.*—About nine inflorescences per lateral branch.

*Inflorescence bud.*—Height: About 7 mm. Diameter: About 1 cm. Color: Close to 143A.

*Inflorescence size.*—Diameter: About 11.7 cm. Depth (height): About 1.9 cm. Diameter of disc: About 3.4 cm. Receptacle diameter: About 7 mm.

*Ray florets.*—Shape: Elongated-oblong. Orientation: Initially upright, then about 80° from vertical. Aspect: Slightly reflexed and slightly twisting. Length: About 5.9 cm. Width: About 1.5 cm. Apex: Acute or emarginate. Base: Attenuate; very short corolla tube. Corolla tube length: About 2 mm. Margin: Entire. Texture: Smooth, glabrous, satiny. Number of ray florets per inflorescence: About 25 arranged in a single row. Color: When opening and fully opened, upper surface: Closest to 155D. When opening and fully opened, lower surface: Closest to 155D.

*Disc florets.*—Arrangement: Massed at center of receptacle, enlarged. Shape: Tubular, elongated. Apex: Five-pointed. Length: About 1.8 cm. Width: Apex: About 6 mm. Base: About 2 mm. Number of disc florets per inflorescence: About 157. Color: Immature: 144A to 154A. Mature: Apex: 5A. Midsection and base: Closest to 155D.

*Peduncles.*—Length: First peduncle: About 7.3 cm. Fourth peduncle: About 11.5 cm. Seventh peduncle: About 13.9 cm. Diameter: About 2 mm. Angle to vertical: About 50 to 55° from vertical. Strength: Moderately strong, flexible. Texture: Pubescent. Color: 146A.

*Reproductive organs.*—Androecium: Present on disc florets only. Anther color: 9A. Pollen: None observed. Gynoecium: Present on both ray and disc florets.

*Seed.*—Seed production has not been observed.

Disease resistance: Resistance to pathogens common to Chrysanthemums has not been observed on plants grown under commercial greenhouse conditions.

It is claimed:

1. A new and distinct cultivar of Chrysanthemum plant named 'White Yograceland', as illustrated and described.

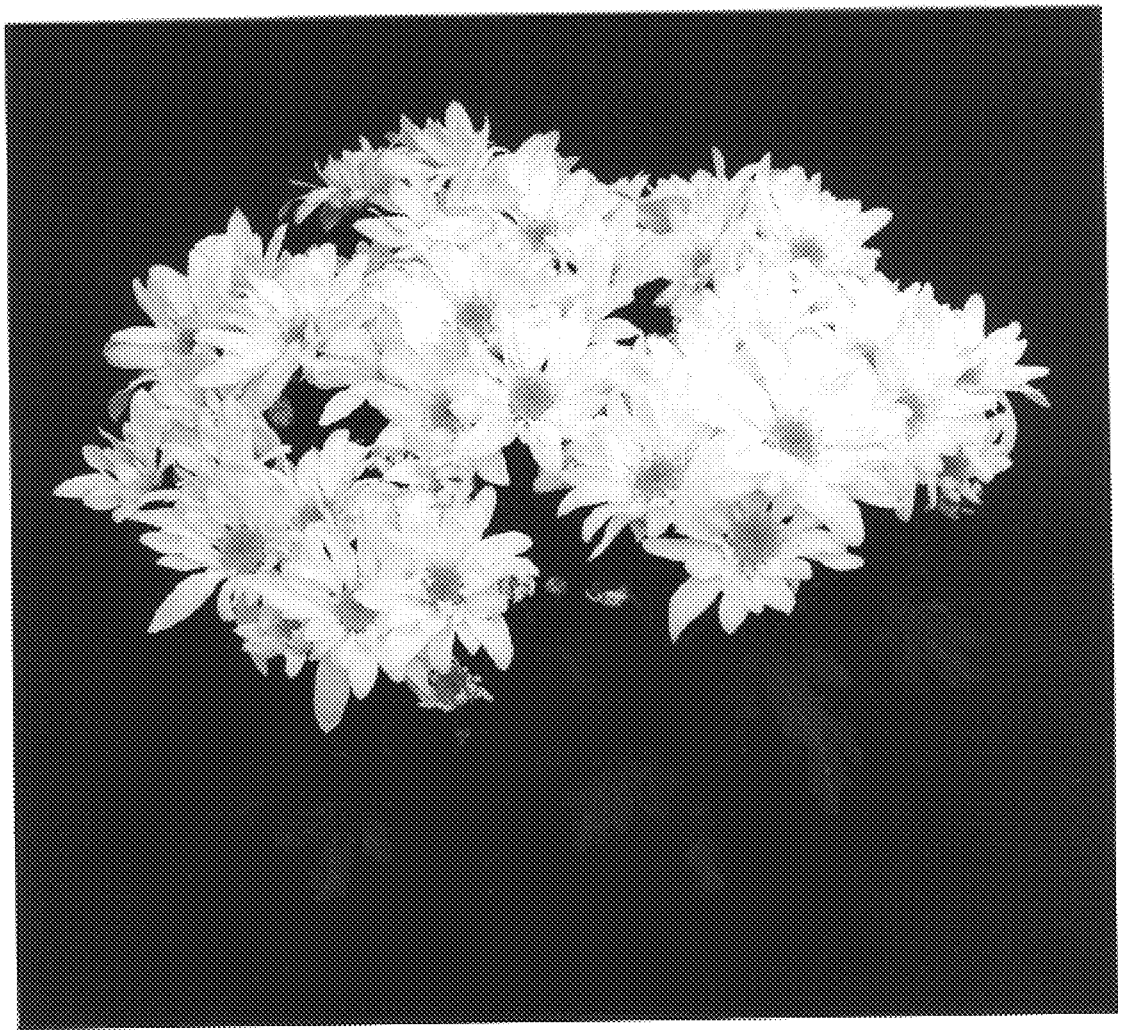

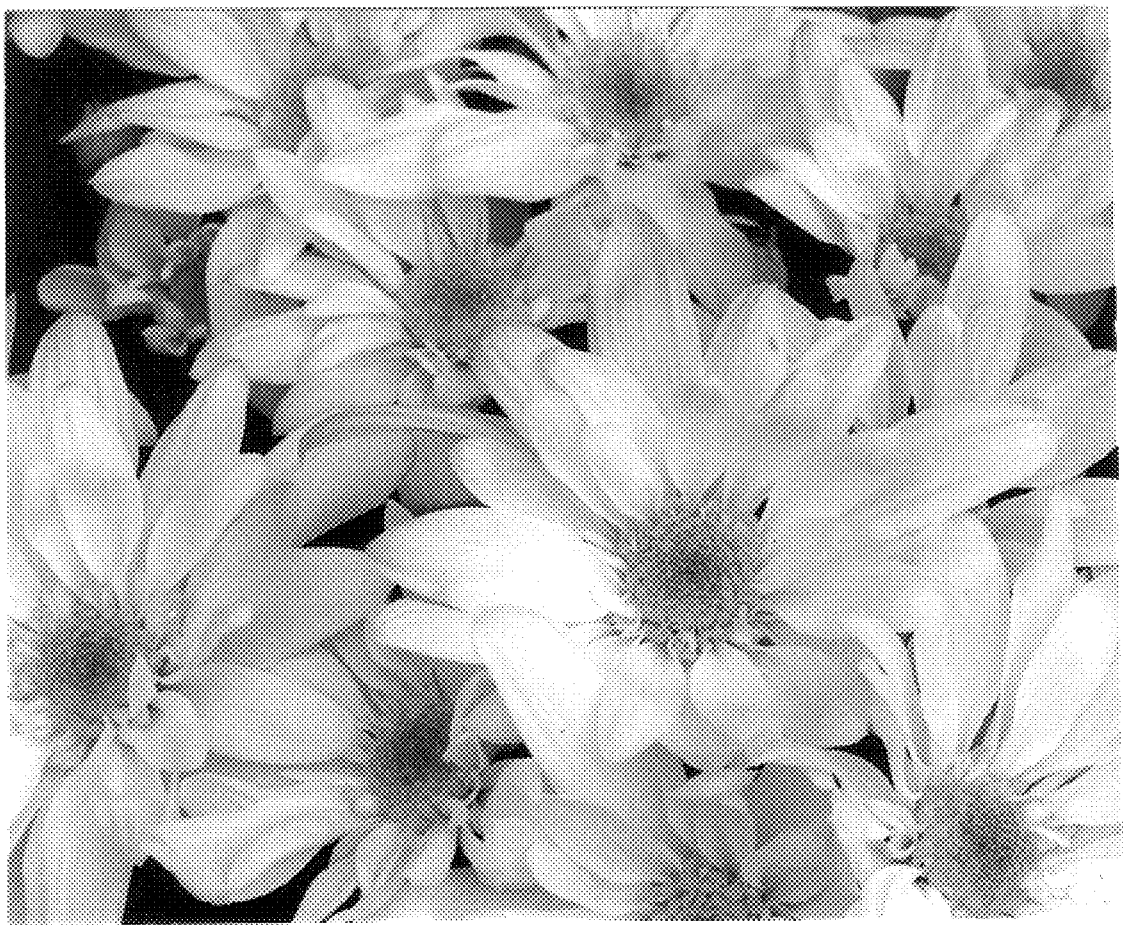

* * * * *